(12) United States Patent
Beck et al.

(10) Patent No.: US 6,509,010 B2
(45) Date of Patent: Jan. 21, 2003

(54) COSMETIC PRODUCTS FOR THE REDUCTION OF SWEAT ACIDITY

(75) Inventors: Jonathan Samuel Beck, Wirral (GB); Jason Shaun Burry, Wirral (GB); Richard Livesey Evans, Wirral (GB); Dominic Granger, Montreal (CA); Raynald Laprade, Montreal (CA); Mireille Marsolais, Montreal (CA)

(73) Assignee: Unilever Home & Personal Care USA, division of Conopco, Inc., Chicago, IL (US)

(*) Notice: Subject to any disclaimer, the term of this patent is extended or adjusted under 35 U.S.C. 154(b) by 0 days.

(21) Appl. No.: 10/066,183

(22) Filed: Jan. 31, 2002

(65) Prior Publication Data

US 2002/0146376 A1 Oct. 10, 2002

(30) Foreign Application Priority Data

Feb. 1, 2001 (GB) .............................. 0102562

(51) Int. Cl.⁷ ............................. A61K 7/32; A61K 7/34; A61K 7/38; A61K 7/00; A61K 3/535; A61K 31/335; A61K 31/35
(52) U.S. Cl. ............................. 424/65; 424/66; 424/68; 424/400; 424/401; 514/288.8; 514/452; 514/460
(58) Field of Search .................... 424/65, 400, 401, 424/66, 68; 514/228.8, 452, 460

(56) References Cited

U.S. PATENT DOCUMENTS

| 3,792,068 A | 2/1974 | Luedders et al. |
| 5,601,809 A | 2/1997 | Davis .......................... 424/65 |
| 5,853,742 A | 12/1998 | Bartolone et al. .......... 424/401 |
| 5,928,671 A | 7/1999 | Domenico ................... 424/653 |
| 6,251,376 B1 | 6/2001 | Beck et al. ................... 424/65 |

FOREIGN PATENT DOCUMENTS

| EP | 689 839 | 1/1996 |
| WO | 00/20043 | 7/1995 |
| WO | 95/20043 | 7/1998 |
| WO | 00/15185 | 3/2000 |
| WO | 00/51589 | 9/2000 |

OTHER PUBLICATIONS

PCT International Search Report in a PCT/EP application 02/00670.
GB Search Report in a GB application GB 0102562.6.

Primary Examiner—Shelley A. Dodson
(74) Attorney, Agent, or Firm—Kevin J. Stein

(57) ABSTRACT

A cosmetic method of reducing the acidity of sweat excreted from human eccrine glands, said method comprising the topical application of a V-ATPase inhibitor to the skin in the vicinity of the eccrine glands. Said method may result in a range of benefits, including enhanced appreciation of topically-applied perfume and enhanced efficacy of topically-applied antiperspirant salt. Cosmetic products and compositions comprising a V-ATPase inhibitor and selected other components are also claimed.

25 Claims, No Drawings

COSMETIC PRODUCTS FOR THE REDUCTION OF SWEAT ACIDITY

FIELD OF INVENTION

This invention relates to cosmetic methods and products concerned with decreasing the acidity of sweat secreted from human eccrine glands, decreasing body malodour, and decreasing perspiration.

BACKGROUND OF INVENTION

Cosmetic deodorant compositions are known. Typical deodorant compositions comprise one or more agents that mask or inhibit the formation of unpleasant body odours; perfumes and/or antimicrobial agents are widely used for this purpose. Some deodorant compositions also reduce perspiration and are termed deodorant antiperspirant compositions, or antiperspirant compositions. Typical antiperspirant compositions comprise a metal antiperspirant salt, such as an astringent aluminium or aluminium/zirconium salt, in combination with a cosmetically suitable vehicle. Such cosmetic deodorant and antiperspirant products are available in a variety of product forms, for example as sticks, roll-on lotions, aerosols and pump spray formulations.

We have discovered a method of gaining a range of benefits, including improved deodorancy and antiperspirancy, by reducing the acidity of sweat secreted by human eccrine glands by topical application of a vacuolar (H+)-ATPase (or V-ATPase) inhibitor. Decreased acidity may result in any of the following benefits: increased desquamation and hence smoother skin (see M. M. Brysk et al, *Experimental Cell Research*, 214(1), 22–26, Sep. 1994); reduced volatility of odiferous short chain fatty acids on the skin surface and hence decreased body malodour; reduced acid-induced damage of cosmetic ingredients applied to the skin, in particular perfumes; and improved performance of antiperspirant compositions comprising an antiperspirant salt.

A method of elevating the pH of human sweat has previously been reported in WO 00/15185 (Beck et al). In this publication, the agent used to increase the pH was a bicarbonate reabsorption inhibitor. The present invention, in contrast, uses a V-ATPase inhibitor. V-ATPase inhibitors are disclosed in numerous publications, including WO 95/20043 (Stein and Tonkinson) and WO 00/51589 (Boyd); however, none of these publications disclose the methods or compositions of the present invention.

The present invention takes advantage of the recent discovery of vacuolar-type H+-ATPases (V-ATPases) in the luminal membrane of eccrine sweat ducts (Bovell D. L., et al, *The Histochemical Journal*, 32, 2000, 409–413).

SUMMARY OF INVENTION

We have found a new method for reducing the acidity of human sweat. The method involves the topical application of a vacuolar (H+)-ATPase (or V-ATPase) inhibitor. Such materials inhibit proton pumps in the luminal membrane of the sweat gland and thereby reduce the sweat gland's ability to acidify the sweat. Significantly, Example 1 of the present patent suggests that not all eccrine sweat ducts have active V-ATPases in the luminal membrane; hence, the present invention discloses a 'selective' method for increasing the pH of sweat secreted from eccrine sweat ducts. Unlike the prior art method involving bicarbonate reabsorption inhibitors (WO 00/15185, Beck et al)., it is believed that the present invention may target sweat ducts producing particularly low pH sweat.

Thus, according to a first aspect of the present invention, there is provided a cosmetic method of reducing the acidity of sweat excreted from human eccrine glands, said method comprising the topical application of a V-ATPase inhibitor to the skin in the vicinity of the eccrine glands.

The higher sweat pH resulting from the use of a V-ATPase inhibitor can lead to enhanced performance of an antiperspirant salt also applied.

Thus, according to a second aspect of the present invention, there is provided a cosmetic method of reducing perspiration, said method comprising the topical application of an antiperspirant salt and a V-ATPase inhibitor to the human skin.

According to a third aspect of the present invention, there is provided a method of enhancing the efficacy of a topically-applied antiperspirant salt, said method comprising the co-application of a V-ATPase inhibitor to the human skin.

According to a fourth aspect of the present invention, there is provided a deodorant product comprising a V-ATPase inhibitor and an antiperspirant salt.

According to a fifth aspect of the present invention, there is provided a method of manufacture of a deodorant composition, said method comprising the mixing of an antiperspirant salt and a V-ATPase inhibitor with a carrier material.

The higher sweat pH resulting from the use of a V-ATPase inhibitor may also lead to enhanced appreciation of topically-applied perfume. This may arise as a result of the perfume smelling better at the higher pH attained; as a result of reduced body malodour resulting from decreased volatility of odiferous fatty acids on the skin surface; as a result of reduced acid-induced damage of said perfume; or as a result of any other mechanism.

Thus, according to a sixth aspect of the present invention, there is provided a cosmetic product comprising a V-ATPase inhibitor and a perfume.

According to a seventh aspect of the present invention, there is provided a method of manufacture of a cosmetic composition, said method comprising the mixing of a perfume and a V-ATPase inhibitor with a carrier material.

DETAILED DESCRIPTION OF THE INVENTION

The elevation of sweat pH brought about by the V-ATPase inhibitor can lead to numerous benefits, as mentioned hereinbefore. For the benefits requiring the co-application of a perfume or an antiperspirant salt, it is not essential that the perfume or antiperspirant salt be applied as part of the same composition as the V-ATPase inhibitor. The benefit may be derived from independent application of the antiperspirant salt or perfume and the V-ATPase inhibitor. Co-application may be concurrent or consecutive, although it is preferred that the V-ATPase inhibitor is applied before or at the same time as the perfume or antiperspirant salt.

In one particular embodiment of the invention, the V-ATPase inhibitor is applied first, such as from a night-time product, for example a cosmetic cream or spray, and a perfume or antiperspirant salt is applied after the luminal membrane proton pump has been inhibited, for example the following morning, from a deodorant composition. In a related embodiment of the invention, the V-ATPase inhibitor is applied from a personal cleansing composition and, after drying, a perfume or antiperspirant salt is applied from a deodorant composition. In a further related embodiment of the invention, the V-ATPase inhibitor and a perfume or antiperspirant salt are simultaneously applied from independent cosmetic compositions. In all products of these types, where the V-ATPase inhibitor and the perfume or antiperspirant salt are applied from independent cosmetic compositions, it is preferred that the product also comprises a means for, and/or instruction for, both of the compositions to be applied to the body.

In another embodiment of the invention, the V-ATPase inhibitor and a perfume or antiperspirant salt are present in the same composition.

Preferred compositions comprising the products of the invention are deodorant compositions, in particular deodorant antiperspirant compositions.

In products comprising a V-ATPase inhibitor and a perfume and/or antiperspirant salt, and in methods of their use, the product is of particular benefit when used on an often malodorous region of the human body, for example the underarm areas or the feet.

Other compositions comprising the products of the invention are skin-care compositions, in particular creams, lotions, and gels.

The V-ATPase Inhibitor

The V-ATPase inhibitor may be any of the materials known in the art to function in this manner. Examples include the V-ATPase inhibitors described in the references cited hereinbefore and incorporated herein by reference. In the present invention, the V-ATPase inhibitor serves to inhibit V-ATPase in the luminal cells of the eccrine sweat gland, particularly the cells of the reabsorptive duct. This leads to a reduction in the rate of proton transfer from within such cells, leading to a decrease in the acidity of the sweat exiting said sweat ducts. When assessed according to the method described in Example 1, preferred materials have a significant effect when present at a level of less than 300 μg/ml, particularly preferred materials have a significant effect when present at a level of less than 100 μg/ml, and especially preferred materials have a significant effect when present at a level of less than 50 μg/ml. Particular V-ATPase inhibitors are selected from the group comprising bafilomycins, concanamycins, olygomycins, oligonucleotides as disclosed in WO 95/20043 (Stein and Tonkinson), prodigiosine, fusiococcin, fusidic acid, suramin, omeprazole, felodipine, and compounds, as described in WO 00/51589 (Boyd), of the formula:

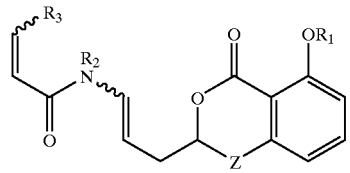

wherein $R_1$ and $R_2$ are the same or different and each is H, a straight-chain or branched saturated or unsaturated alkyl, an aryl, R $CH_2$—, R CO—, or R $SO_2$—, wherein R is H, a straight-chain or branched saturated or unsaturated alkyl, or an aryl; $R_3$ is H, a straight-chain or branched saturated or unsaturated alkyl, an aryl, an oxime, or an oxime methyl ether; the aromatic ring is unsubstituted or substituted with at least one substituent selected from the group consisting or a halogen, a nitro, an amino, a hydroxyl, a thio, an acyl, an alkyl, and a cyano; the saturated alkyl, unsaturated alkyl and aryl substituents defined in $R_1$—$R_3$ and R are unsubstituted or substituted with at least one substituent selected from the group consisting of a halogen, a nitro, an amino, a hydroxyl, a thio, an acyl, an alkyl, and a cyano; and Z is a contiguous linker comprising a chain of 0–12 atoms which, together with the five atoms beginning with the carbon or the aromatic ring in meta-relationship with $OR_1$ and ending with the carbon directly attached to the alkyl oxygen of the lactone, said carbons being covalently bonded to either end of linker Z, integrally form a 5–17 membered ring; or a salt or ester thereof. Preferred V-APTase inhibitors of this formula are salicylihalamides A and B, lobatamides A–F, and apicularen A and B.

Preferred V-ATPase inhibitors are bafilomycins (especially bafilomycin $A_1$), concanamycins (especially concanamycin A,) and olygomycin. Preferred materials having large-scale commercial availability are omeprazole and felodipine.

In some circumstances, it is preferred that the V-ATPase inhibitor is present in or derived from a natural extract. The preferred level of incorporation of V-ATPase inhibitor into a composition greatly depends upon the effectiveness of the V-ATPase inhibitor employed and the dose typically delivered to the skin by said composition. Typical levels are from 0.05% to 10% by weight of the composition of which it is a part. (In calculating the level of V-ATPase inhibitor present in a composition, any volatile propellant present is not taken into account in the calculation). It is preferred that the aforementioned level is 0.1% or greater and it is particularly preferred that the level is 0.5% or greater. With regard to the maximum amount employed, it is preferred that this is no greater than 5% and particularly preferred that the level is no greater than 1% by weight.

Additional Components

Antiperspirant Salt

Conventional inorganic antiperspirant salts may be used in the products of the invention. Examples include astringent active salts, in particular, aluminium, zirconium and mixed aluminium/ zirconium salts, including both inorganic salts, salts with organic anions and complexes. Preferred astringent salts include aluminium, zirconium and aluminium/zirconium halides and halohydrate salts, such as chlorohydrates. Preferred levels of incorporation are from 0.5% to 60%, particularly from 5% to 30% or 40% and especially from 5% or 10% to 30% or 35% by weight of the composition of which it is a part. In non-aqueous formulations, the above weight percentages exclude any water of hydration bound to the antiperspirant salt. Especially preferred aluminium halohydrate salts, known as activated aluminium chlorohydrates (ACCH), are described in EP 6,739 (Unilever PLC and NV). Zirconium aluminium chlorohydrate (ZACH) salts are also preferred materials, as are the so-called ZAG (zirconium-aluminium-glycine) complexes, for example those disclosed in U.S. Pat. No. 3,792,068 (Procter and Gamble Co.) and activated versions called AZAG.

When an antiperspirant salt is employed, the weight ratio of antiperspirant salt to V-ATPase inhibitor is generally quite high: typically between 300:1 and 2:1. Preferably the weight ratio is between 100:1 and 5:1 and particularly preferred is a ratio between 50:1 and 10:1.

Carrier Material

A carrier material for the antiperspirant salt and/or the V-ATPase inhibitor, is a preferred additional component in the products of the invention. The carrier material may be hydrophobic or hydrophilic, solid or liquid. Preferred carrier materials are liquids at ambient temperature and atmospheric pressure. Hydrophobic liquids suitable for use include liquid silicones, that is to say, silicone oils. Such materials have desirable sensory properties, making them particularly preferred, especially in skin-care compositions. The liquid silicones may be cyclic or linear, examples include Dow Corning silicone fluids 344, 345, 244, 245, 246, 556, and the 200 series; Union Carbide Corporation Silicones 7207 and 7158; and General Electric silicone SF1202. Alternatively, non-silicone hydrophobic liquids may be used. Such materials include mineral oils, hydrogenated polyisobutene, polydecene, paraffins, isoparaffins of at least 10 carbon atoms, and aliphatic or aromatic ester oils (eg. isopropyl myristate, lauryl myristate, isopropyl palmitate, diisopropyl sebecate, diisopropyl adipate, or $C_8$ to $C_{18}$ alkyl benzoates).

Hydrophilic liquid carrier materials, for example water, may also be employed. Systems employing water are often emulsion systems having an aqueous phase (typically 40 to 80% by weight) and a non-aqueous phase (typically 20 to 60% by weight).

Particularly preferred liquid carrier materials comprise organic solvents. Preferred organic solvents have a melting point of less than 10° C., preferably less than 5° C.; this can benefit both low temperature storage stability and ease of manufacture. A class of preferred organic solvents are aliphatic alcohols (monohydric or polyhydric, preferably having 2 to 8 carbon atoms) and polyglycol ethers, preferably oligoglycol ethers having only 2 to 5 repeat units. Examples include dipropylene glycol, glycerol propylene glycol, butylene glycol, ethanol, propanol, isopropanol, and industrial methylated spirits. The most preferred organic solvents are aliphatic alcohols, in particular those having 2 to 3 carbon atoms, especially ethanol and isopropanol.

Mixtures of carrier materials may also be used. The amount of carrier material employed is preferably from 30% to 99%, more preferably 60% to 98%, of the composition, excluding any volatile propellant that may be present.

When organic solvent is present in a composition, it is often present at from 30% to 98% by weight of the total weight of the liquid components of the composition; in particular, the organic solvent often comprises from 60% to 97% by weight of the total liquids present.

Additional Anti-microbial Agent

An additional component that can sometimes augment the ability of the compositions of the invention to reduce body odour is an anti-microbial agent. Most of the classes of agents commonly used in the art can be incorporated into compositions of the invention. Levels of incorporation are preferably from 0.01% to 3%, more preferably from 0.03% to 0.5% by weight of the composition, excluding any volatile propellant that may be present.

Preferred anti-microbial agents have a minimum inhibitory concentration (MIC) of 1 mg.ml$^{-1}$ or less, particularly 200 µg.ml$^{-1}$ or less, and especially 100 µg.ml$^{-1}$ or less. The MIC of an anti-microbial agent is the minimum concentration of the agent required to significantly inhibit microbial growth. Inhibition is considered significant if an 80% or greater reduction in the growth of an inoculum of a relevant micro-organism is observed, relative to a control medium without an anti-microbial agent, over a period of 16 to 24 hours at 37° C. A relevant micro-organism that may be used is *Staphylococcus epidermidis*. Details of suitable methods for determining MICs can be found in Antimicrobial Agents and Susceptibility Testing, C. Thornsberry, (in *Manual of Clinical Microbiology*, 5$^{th}$ Edition, Ed. A. Balows et al, *American Society for Microbiology*, Washington D.C., 1991). A particularly suitable method is the Macrobroth Dilution Method, as described in Chapter 110 of above publication (pp. 1101–1111) by D. F. Sahm and J. A. Washington II. MICs of anti-microbials suitable for inclusion in the compositions of the invention are triclosan: 0.01–10 µg.ml$^{-1}$ (J.Regos et al., *Dermatologica* (1979), 158: 72–79) and farnesol: ca. 25 µg.ml$^{-1}$ (K. Sawano, T. Sato, and R. Hattori, Proceedings of the 17$^{th}$ IFSCC International Conference, Yokahama (1992) p.210–232). By contrast ethanol and similar alkanols have MICs of greater than 1 mg.ml$^{-1}$. Preferred anti-microbials are bactericides, in particular organic bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in Deodorant Ingredients , S. A.Makin and M. R.Lowry, in Antiperspirants and Deodorants , Ed. K. Laden (1999, Marcel Dekker, New York). More preferred anti-microbials for use in the compositions of the invention are polyhexamethylene biguanide (PHMB) salts (also known as polyaminopropyl biguanide salts), an example being Cosmocil CQ available from Zeneca PLC, preferably used at up to 1% and more preferably at 0.03% to 0.3% by weight; 2',4,4'-trichloro,2-hydroxy-diphenyl ether (triclosan), preferably used at up to 1% by weight and more preferably at 0.05–0.3% by weight of the non-volatile components of the composition; and 3,7,11-trimethyldodeca-2,6,10-trienol (farnesol), preferably used at up to 1% and more preferably at up to 0.5% by weight of the non-volatile components of the composition.

Inorganic antimicrobial agents may also be employed, for example zinc phenol sulphonate, preferably at up to 3% by weight of the non-volatile components of the composition.

Structurants and Emulsifiers

Structurants and emulsifiers are further additional components of the compositions of the invention that are highly desirable in certain product forms. Structurants, when employed, are preferably present at from 1% to 30% by weight of the composition, whilst emulsifiers are preferably present at from 0.1% to 10% by weight of the composition. In roll-ons, such materials help control the rate at which product is dispensed by the roll ball. In stick compositions, such materials can form gels or solids from solutions or suspensions of the chelator salt in a carrier fluid. Suitable structurants for use in such compositions of the invention include cellulosic thickeners such as hydroxypropyl cellulose and hydroxy ethyl cellulose, and dibenzylidene sorbitol. Emulsion pump sprays, roll-ons, creams, and gel compositions according to the invention can be formed using a range of oils, waxes, and emulsifiers. Suitable emulsifiers include steareth-2, steareth-20, steareth-21, ceteareth-20, glyceryl stearate, cetyl alcohol, cetearyl alcohol, PEG-20 stearate, and dimethicone copolyol. Suspension aerosols, roll-ons, sticks, and creams require structurants to slow sedimentation (in fluid compositions) and to give the desired product consistency to non-fluid compositions. Suitable structurants include sodium stearate, stearyl alcohol, cetyl alcohol, hydrogenated castor oil, synthetic waxes, paraffin waxes, hydroxystearic acid, dibutyl lauroyl glutamide, beta-sitosterol, oryzanol, acylated cellobiose, alkyl silicone waxes, quaternium-18 bentonite, quaternium-18 hectorite, silica, and propylene carbonate. Some of the above materials also function as suspending agents in certain compositions.

Further emulsifiers desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers or esters, often comprising 5 to 30 oxyethylene units and a C10 to C22 alkyl or acyl chain.

Sensory Modifiers

Certain sensory modifiers are further desirable components in the compositions of the invention. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (eg. Aerosil 200), polyethylene (eg. Acumist B18), polysaccharides, corn starch, C12-C15 alcohol benzoate, PPG-3 myristyl ether, octyl dodecanol, C7-C14 isoparaffins, di-isopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane. Liquid emollients, including silicone oils, and humectants, are of particular benefit in compositions of the present invention, especially in skin-care compositions.

Perfume

Perfume is a key component in many of the products of the invention. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight of the composition in which the perfume is present, excluding any volatile propellant that may be present in said composition. In certain embodiments, these preferred levels of perfume incorporation apply by weight of the total composition, that is to say, including any volatile propellant that may also be present.

Additional pH Modifiers

In some products it may be preferred to incorporate an additional pH modifier, in order to assist the V-ATPase inhibitor in reducing the acidity of the sweat upon the skin surface. Simple bases, such as bicarbonate, may be employed. Alternatively, or additionally, a bicarbonate reabsorption inhibitor as described in WO 00/15185 (Beck et al) may be employed.

Further Additional Components

Further additional components that may also be included are colourants and preservatives, for example $C_{1-C3}$ alkyl parabens.

Product Forms

The compositions comprising the products of the invention may take any form. Examples include wax-based sticks, soap-based sticks, compressed powder sticks, roll-on suspensions or solutions, emulsions, gels, creams, squeeze sprays, pump sprays, and aerosols. Each product form contains its own selection of additional components, some essential and some optional. The types of components typical for each of the above product forms may be incorporated in the corresponding compositions of the invention. Roll-on compositions particularly suited to the invention are simple solutions in organic solvents, although water can be tolerated in such compositions. In addition, emulsion compositions, for example oil-in-water and water-in-oil emulsions, are not excluded. Stick compositions of the invention are preferably based on either a monohydric or polyhydric alcohol organic solvent base. They are often gelled with sodium stearate, although dibenzylidene sorbitol (DBS) may alternatively be used, preferably in combination with hydroxypropyl cellulose.

Aerosol compositions of the invention may comprise from 30 to 99 parts by weight, and particularly 30 to 60 parts by weight of propellant and the remainder (respectively 70 to 1 and particularly 70 to 40 parts by weight) of the antiperspirant/deodorant base composition.

The propellant in the aerosol compositions may be selected from liquified hydrocarbons or halogenated hydrocarbon gases (particularly fluorinated hydrocarbons such as 1,1-difluoroethane and/or 1-trifluoro-2-fluoroethane) that have a boiling point of below 10° C. and especially those with a boiling point below 0° C. It is especially preferred to employ liquified hydrocarbon gases, and especially $C_3$ to $C_6$ hydrocarbons, including propane, isopropane, butane, isobutane, pentane and isopentane and mixtures of two or more thereof. Preferred propellants are isobutane, isobutane/isopropane, isobutane/propane and mixtures of isopropane, isobutane and butane. Other propellants that can be contemplated include alkyl ethers, such as dimethyl ether or compressed non-reactive gasses such air, nitrogen or carbon dioxide.

The means of application of the V-ATPase inhibitor and/or other optional components of the invention may be directly from one of the aforementioned product forms or it may be indirect, via preliminary application to paper towelling or fabric. Thus, the V-ATPase inhibitor could be applied from a paper or fabric wipe, drawn across the skin surface and thereby transferring V-ATPase inhibitor from the wipe to the skin. Alternatively, the V-ATPase inhibitor could be applied by some other means and a composition comprising a perfume or an antiperspirant salt applied via a wipe.

Methods of Manufacture

The compositions comprising the products of the invention may be manufactured by any convenient method. In a particular embodiment of present invention, a suitable composition is manufactured by the mixing of a V-ATPase inhibitor and a perfume and/or antiperspirant salt with an appropriate carrier material, the components being agitated to give a homogeneous mixture. Said mixture may be used in any of the product forms described above, with the incorporation of the appropriate additional components.

EXAMPLES

Example 1

Proton Transfer Inhibition by a V-ATPase Inhibitor

Human eccrine sweat ducts were isolated using the Kealey shearing technique (Lee C. M., Jones C. J., and Kealey T., *J. Cell. Sci.*, 72, 1984, 259–274). Isolated portions of reabsorptive duct were mounted on a conventional microperfusion apparatus, between glass pipettes. One end of the duct was cannulated with a microperfusion pipette. The ducts were perfused at 37° C. with a control solution containing N-methyl-D-glucamine chloride (114 mM), potassium hydrogenphosphate (2.5 mM), magnesium chloride (1 mM), calcium chloride (1 mM), glucose (5 mM), and N-methyl-D-glucamine lactate (4 mM). Osmolality was adjusted to 300 mOsm/kg with mannitol and the pH adjusted to 7.4 with tris-HEPES. Intracellular pH was measured using the pH sensitive fluorescent probe BCEFC (bis-2-carboxyethyl-carbfluorescein) at 5 $\mu$M.

In order to investigate the effect of V-ATPase inhibitors, the intracellular pH was first rapidly decreased from its equilibrium value by a 20 mM basolateral pulse of ammonium chloride (pulse duration: 30 to 60 sec.). Intracellular pH was monitored and two kinds of response were observed: either the sweat duct exhibited a steady pH recovery or the sweat duct exhibited no significant pH recovery. The former response was most prevalent. The sweat ducts exhibiting this behaviour were selected for the next part of the procedure.

In the next part of the procedure, the indicated sweat ducts were subjected to acidification by a 20 mM basolateral pulse of ammonium chloride, with the additional presence of a V-ATPase inhibitor. The results, as indicated in Table 1, show that ATPase inhibitors lead to a significant reduction in the rate of pH recovery, compared with the control. Hence, olygomycin (at 20 $\mu$g/ml), bafilomycin-$A_1$ (at 6.2 $\mu$g/ml), and concanamycin-A (at 0.1 $\mu$g/ml) all inhibit proton transfer out of the cells of the reabsorptive duct. These results are all significant at the 95% level (as determined by the Student t-test).

TABLE 1

| V-ATPase Inhibitor | Conc. ($\mu$g/ml) | Rate of pH recovery (%) |
|---|---|---|
| None (control) | — | 100 |
| Olygomycin | 20 | 12 |
| Bafilomycin-$A_1$ | 6.2 | 27 |
| Concanamycin-A | 0.1 | 5 |

Examples 2 to 7

Deodorant Compositions

The following represent typical deodorant compositions incorporating a V-ATPase at a level of 0.1% to 5% by weight of the composition, excluding any volatile propellant that may be present. The figures refer to percentages by weight of the total composition.

TABLE 2

| | Aerosol Compositions | | | | | |
|---|---|---|---|---|---|---|
| Example: | 2.1 | 2.2 | 2.3 | 2.4 | 2.5 | 2.6 |
| Cyclomethicone (DC245) | 3.47 | 11.8 | 14.4 | 3.55 | 4.1 | 5.2 |
| Ethanol | | | 20 | | | |
| Isopropyl palmitate | | | 10.3 | | 8.5 | |
| Isopropyl myristate | | | | | | 0.31 |
| PPG-14 butyl ether | 9.7 | 0.7 | | | | 9.1 |
| Octyldodecanol | | 0.25 | | | | |
| Polydecene | | | | | | 0.3 |
| Dibutyl phthalate | | | | | 4.5 | |
| Bentone 38 (ex Rheox) | 1 | 1 | 1.5 | 1 | 0.95 | 0.7 |
| Propylene carbonate | | | | | 0.15 | |
| Methylpropanolamine | | | | | | 0.08 |
| Silicone gum (Q2-1401) | | | | 0.2 | | |
| AACH | | 10 | | 4 | | |
| Milled AACH | 10 | | | | | 2 |
| ACH | | | 9.2 | | 9.3 | |
| Silica | | 0.1 | | | | 0.01 |
| Talc | | | 3 | | | |
| Micronised polyethylene | | | | | 9.3 | |
| Perfume | 0.5 | 0.7 | 0.7 | 0.7 | | 1 |
| Allantoin | | | | | 1.5 | |
| Palmitoyl ethanolamide | 0.3 | 0.3 | 0.3 | 0.3 | 0.3 | 0.3 |
| V-ATPase inhibitor | 0.03 | 0.15 | 0.6 | 0.25 | 1.4 | 1 |
| n-Pentane | | | | | 20 | |
| C3/C4 hydrocarbons | 75 | 75 | 40 | 70 | 60 | 80 |

TABLE 3

| | Lotion Compositions | | | | | | | | |
|---|---|---|---|---|---|---|---|---|---|
| Example: | 3.1 | 3.2 | 3.3 | 3.4 | 3.5 | 3.6 | 3.7 | 3.8 | 3.9 |
| Ethanol | | 30 | | 60 | | | | 28 | |
| Isopropanol | 30 | | 30 | | 30 | 60 | 30 | | |
| Hydroxypropyl-cellulose | 0.7 | 0.7 | 0.7 | 0.7 | 0.7 | 0.7 | 0.7 | 0.7 | |
| ACH | | 4 | 4 | | | | 20 | | |
| ZACH | | | | | | | | | 20 |

TABLE 3-continued

Lotion Compositions

| Example: | 3.1 | 3.2 | 3.3 | 3.4 | 3.5 | 3.6 | 3.7 | 3.8 | 3.9 |
|---|---|---|---|---|---|---|---|---|---|
| AZAG | | | | | | | | | 18 |
| PHMB | | | | 0.2 | 0.2 | | | | |
| Triclosan | | | | | | 0.1 | | | |
| Suspending Agent | | | | | | | | | 3 |
| Propylene Carbonate | | | | | | | | | 1 |
| Talc | | | | | | | | | 6 |
| V-ATPase inhibitor | 0.2 | 0.4 | 0.6 | 0.8 | 1 | 2 | 3 | 4 | 5 |
| Water + minors | 69.1 | 64.9 | 64.7 | 38.3 | 68.1 | 37.2 | 46.3 | 47.3 | |
| Cyclomethicone + minors | | | | | | | | | 67 |
| | | | | | | | | | 15 |

TABLE 4

Cream and Soft Solid Compositions

| Example: | 4.1 | 4.2 | 4.3 | 4.4 | 4.5 |
|---|---|---|---|---|---|
| C18–C36 acid glycol ester | | 2.5 | | 3.75 | |
| Castor wax | | 7.5 | | 1.25 | |
| Triacontenyl vinyl pyrrolidone copolymer | 5 | | | | |
| Paraffin wax | 5 | | | | |
| Silica | | 1 | | | 0.2 |
| Cyclopentasiloxane and cetearyl-dimethicone/vinyl dimethicone co-polymer | | | | | 64.05 |
| C12–15 alkyl benzoate | 64.3 | 63.1 | 62.9 | 63.7 | 4 |
| Dextrin palmitate | | | 10 | 5 | |
| Neopentyl glycol diheptanoate | | | | | 5 |
| PEG-8 distearate | | | | | 2 |
| Stearyl dimethicone | | | | | 0.75 |
| AACH | 25 | | | 25.5 | |
| Milled AACH | | 25.5 | 26 | | |
| AZAG | | | | | 22 |
| V-ATPase inhibitor | 0.2 | 0.4 | 0.6 | 0.8 | 1.5 |
| Perfume | | 0.5 | | 0.5 | 0.5 |

TABLE 5

Further Cream and Soft Solid Compositions

| Examples: | 5.1 | 5.2 | 5.3 | 5.4 | 5.5 | 5.6 | 5.7 | 5.8 |
|---|---|---|---|---|---|---|---|---|
| Silicone wax | 2.5 | | | 3 | | | | |
| N-lauroyl glutamic acid dibutylamide | | 1 | | | | | | |
| C18—C36 acid glycol ester | | | 5 | | | | | |
| C18—C36 acid triglyceride | | | | 1.25 | | | | |
| Castor wax | | | | | | | 4 | |
| Stearyl alcohol | | | | | | | 6 | |
| Paraffin wax | 7.5 | | | | | | | |
| Candelilla wax | | | | | | | 7 | |
| C24/28 alkyl dimethicone wax | | | | | | | 3.5 | |
| Silica | | | | 1.5 | 1.5 | | | |
| Talc | | | | 1.75 | 6 | 5 | | |
| Bentone 38 | | | | | 3 | | 0.5 | |
| Anhydrous aluminium silicate | | | | | 6 | | | |
| Microthene powder | | | | | 6 | | | |
| Propylene carbonate | | | | | 1.5 | | | |
| Cyclomethicone | 64.4 | | 61 | 62.5 | 36.3 | 56 | 43 | 47.8 |
| Tetraphenyl tetramethylsiloxane | | 52.7 | | | | | | |
| C12–15 Alkyl benzoate | | | | | 10 | | | 11.7 |
| Dextrin palmitate | | 5 | | | | | | 9 |
| Octyldodecanol | | 15 | | | | | | |
| PPG14 butyl ether | | | | | | 4.5 | | |
| Dimethicone (10 cst.) | | | 5 | | 10 | | | |
| Dimethicone (350 cst.) | | | | | | | | 24 |
| POE-100 stearyl ether | | | | | 2 | | | |
| POE-100 stearate | | | | | | | 1 | |
| AACH | 25.5 | | 22 | | | | | |

TABLE 5-continued

Further Cream and Soft Solid Compositions

| Examples: | 5.1 | 5.2 | 5.3 | 5.4 | 5.5 | 5.6 | 5.7 | 5.8 |
|---|---|---|---|---|---|---|---|---|
| Milled AACH |  | 25.5 |  |  |  |  |  |  |
| ACH |  |  |  |  |  |  | 18 |  |
| AZAG |  |  | 25 |  | 25.7 | 20 |  | 26.5 |
| V-ATPase inhibitor | 0.1 | 0.3 | 0.5 | 1 | 2 | 3 | 4 | 5 |
| Perfume |  | 0.5 | 0.5 |  |  | 0.5 |  |  |

TABLE 6

Solid Stick Compositions

| Examples: | 6.1 | 6.2 | 6.3 | 6.4 | 6.5 | 6.6 |
|---|---|---|---|---|---|---|
| Cyclomethicone (DC245) | 40.7 | 37.3 | 40.1 | 39.75 | 45.5 |  |
| Permethyl 103A | 16 | 12 |  |  |  |  |
| PPG-14 Butyl ether |  |  | 4 | 10 |  |  |
| Propylene glycol |  |  |  |  |  | 47.8 |
| Ethanol |  |  |  |  |  | 13 |
| Isostearyl alcohol |  |  |  |  |  | 12 |
| Stearyl alcohol | 14 | 14 | 17 | 11.5 |  |  |
| Castor wax | 2 | 5 | 2.5 | 5 |  |  |
| 12-hydroxystearic acid |  |  |  |  | 6 |  |
| N-lauroyl glutamic acid dibutylamide |  |  |  |  | 2 |  |
| Dibenzyilidene sorbitol |  |  |  |  |  | 3 |
| Eicosanol | 0.2 | 0.2 |  |  |  |  |
| Octyldodecanol |  |  |  | 14 | 14 |  |
| C20–40 alcohols |  |  |  |  | 0.5 |  |
| C20–40 pareth-3/C20–40 pareth-20 |  |  |  |  | 1.75 |  |
| PEG-8 distearate |  |  |  | 0.6 | 5 |  |
| Amino-2-methyl-1-propanol |  |  |  |  |  | 0.2 |
| Al-Zr Gly antiperspirant salt | 23 | 25 | 24 | 26 | 26 | 22.5 |
| Glycerol |  |  | 2 |  |  |  |
| EDTA |  |  |  | 1 |  |  |
| Talc | 3 |  |  |  |  |  |
| Fumed silica |  | 1 | 2 |  |  |  |
| Perfume | 1 | 1 | 1 |  |  |  |
| V-ATPase inhibitor | 0.1 | 0.5 | 0.8 | 1 | 1 | 1.5 |

TABLE 7

Further Solid Stick Compositions

| Examples: | 7.1 | 7.2 | 7.3 | 7.4 | 7.5 | 7.6 |
|---|---|---|---|---|---|---|
| Cyclomethicone (DC245) | 36.3 | 49.25 | 10 | 37 |  |  |
| Mineral oil | 11.5 |  |  |  |  |  |
| Polydecene |  |  | 12.7 |  |  |  |
| PPG-14 butyl ether |  |  | 2.5 |  |  |  |
| C12–15 alkyl benzoate |  |  |  | 15 |  |  |
| Dimethicone (50 cst.) | 1.5 |  |  |  |  |  |
| Propylene glycol |  |  |  |  | 31 | 53.5 |
| Ethanol |  |  |  |  | 50 |  |
| Water |  |  |  |  | 8.7 | 20 |
| Stearyl alcohol | 14 |  |  |  | 1 |  |
| Castor wax | 4.5 |  |  |  |  |  |
| Dextrin palmitate |  | 10 |  |  |  |  |
| Cellobiose octanonanoate |  |  | 3.8 |  |  |  |
| Beta sitosterol |  |  |  | 2.5 |  |  |
| Oryzanol |  |  |  | 2.5 |  |  |
| Sodium stearate |  |  |  |  | 5.8 | 7.7 |
| Eicosanol | 0.2 |  |  |  |  |  |
| Isopropyl myristate |  | 10 |  |  |  |  |
| Cetyl dimethicone copolyol |  |  | 1 | 1 |  |  |
| Amino-2-methyl-1-propanol |  |  |  |  |  | 0.5 |
| Poloxamer 407 |  |  |  |  |  | 6 |
| Cocamide DEA |  |  |  |  |  | 7 |
| Aluminium chlorohydrate | 26 | 30 |  |  |  |  |
| Zirkonal 50 |  |  |  | 51.7 | 40 |  |
| Triclosan |  |  |  |  |  | 0.3 |
| Glycerol | 2 |  | 17.3 |  |  |  |
| Talc | 1.5 |  |  |  |  |  |
| Fumed silica | 1 |  |  |  |  |  |
| Perfume | 1 |  |  |  |  |  |
| V-ATPase inhibitor | 0.5 | 0.75 | 1 | 2 | 3.5 | 5 |

What is claimed is:

1. A cosmetic method of reducing the acidity of sweat excreted from human eccrine glands, said method comprising the topical application of a V-ATPase inhibitor to the skin in the vicinity of the eccrine glands.

2. A cosmetic method of reducing perspiration, said method comprising the topical application of an antiperspirant salt and a V-ATPase inhibitor to the human skin.

3. A method of enhancing the efficacy of a topically-applied antiperspirant salt, said method comprising the co-application of a V-ATPase inhibitor to the human skin.

4. A method according to claim 2, said method comprising the topical application of an antiperspirant composition comprising both an antiperspirant salt and a V-ATPase inhibitor to the human skin.

5. A method according to claim 2, said method comprising the topical application of a cosmetic composition comprising a V-ATPase inhibitor, followed by the topical application of an antiperspirant composition comprising an antiperspirant salt.

6. A method according to claim 1, said method comprising topical application to the underarm areas or to the feet.

7. A method according to claim 1, said method resulting in reduced body malodour.

8. A method according to claim 1, comprising the topical application of a V-ATPase inhibitor selected from the group consisting of bafilomycins, concanamycins, olygomycins, salicylihalamides A and B, lobatamides A–F, and apicularens A and B.

9. A method according to claim 8, comprising the topical application of a V-ATPase inhibitor selected from the group consisting of bafilomycin $A_1$, concanamycin A, and olygomycin.

10. A method according to claim 1, comprising the topical application of a V-ATPase inhibitor selected from the group consisting of omeprazole and felodipine.

11. A method according to claim 1, also comprising the application of a perfume to the human skin.

12. A method according to claim 1, also comprising the application of a liquid emollient or humectant to the human skin.

13. A cosmetic product comprising a V-ATPase inhibitor and a perfume.

14. A cosmetic product according to claim 13, comprising a cosmetic composition comprising both a V-ATPase inhibitor and a perfume.

15. A cosmetic product according to claim 13, comprising a cosmetic composition comprising a V-ATPase inhibitor and an independent cosmetic composition comprising a perfume.

16. A cosmetic product comprising a V-ATPase inhibitor and a liquid emollient or humectant.

17. A cosmetic product according to claim 16, comprising a cosmetic composition comprising both a V-ATPase inhibitor and a liquid emollient or humectant.

18. A deodorant composition comprising a V-ATPase inhibitor and an antiperspirant salt.

19. A deodorant product according to claim 18, comprising a deodorant composition comprising both a V-ATPase inhibitor and an antiperspirant salt.

20. A deodorant product according to claim 18, comprising a cosmetic composition comprising a V-ATPase inhibitor and an independent deodorant composition comprising an antiperspirant salt.

21. A deodorant product according to claim 18, wherein the antiperspirant salt is an aluminium, zirconium, or mixed aluminium/zirconium astringent active salt.

22. A product according to claim 18, comprising a composition comprising a carrier material.

23. A product according to claim 14, comprising a composition comprising an antimicrobial agent that is not itself an antiperspirant salt.

24. A method of manufacture of a cosmetic composition, said method comprising the mixing of a perfume and a V-ATPase inhibitor with a carrier material.

25. A method of manufacture of a deodorant composition, said method comprising the mixing of an antiperspirant salt and a V-ATPase inhibitor with a carrier material.

* * * * *